(12) United States Patent
Ghannad et al.

(10) Patent No.: US 7,708,021 B2
(45) Date of Patent: May 4, 2010

(54) COMPOSITION AND METHOD FOR SIMULTANEOUSLY LIGHTENING AND COLORING HAIR

(75) Inventors: Ali D. Ghannad, The Woodlands, TX (US); Farouk M. Shami, The Woodlands, TX (US)

(73) Assignee: Farouk Systems, Inc., Houston, TX (US)

( * ) Notice: Subject to any disclaimer, the term of this patent is extended or adjusted under 35 U.S.C. 154(b) by 0 days.

(21) Appl. No.: 11/652,833

(22) Filed: Jan. 12, 2007

(65) Prior Publication Data

US 2007/0251538 A1    Nov. 1, 2007

Related U.S. Application Data

(60) Provisional application No. 60/758,954, filed on Jan. 13, 2006.

(51) Int. Cl.
| | |
|---|---|
| *A61Q 5/10* | (2006.01) |
| *A61Q 5/08* | (2006.01) |
| *A61K 8/04* | (2006.01) |
| *A61K 8/22* | (2006.01) |
| *A61K 8/49* | (2006.01) |
| *A61K 8/92* | (2006.01) |

(52) U.S. Cl. .......... 132/208; 424/62; 252/186.1; 252/186.41; 8/102; 8/110; 8/111; 8/426; 8/639; 8/662

(58) Field of Classification Search .......... None
See application file for complete search history.

(56) References Cited

U.S. PATENT DOCUMENTS

| | | | | |
|---|---|---|---|---|
| 4,170,637 | A * | 10/1979 | Pum ............................ | 424/62 |
| 6,440,177 | B1 * | 8/2002 | Orr .............................. | 8/426 |
| 6,746,492 | B2 * | 6/2004 | Kawai et al. ................. | 8/405 |
| 2005/0257328 | A1 * | 11/2005 | Sallwey et al. ............... | 8/405 |

OTHER PUBLICATIONS

"Formulation Enhancement Through The Use of Gelled Emollients", by David S. Morrison, Ph.D. and Gina Butuc, Penreco Technology Center, Woodlands, Tex, pp. 239-244, 1997.*
Optima Specialty Chemical, "Isohexadecane, Isododecane, Isoeicosane" webpage, accessed through www.archive.org (Dec. 30, 2005 archive): http://web.archive.org/web/20051230155316/http://www.optimaspecialty.com/itm00005.htm ; accessed Jun. 5, 2009.*

* cited by examiner

*Primary Examiner*—Yvonne L Eyler
*Assistant Examiner*—Christopher R Lea
(74) *Attorney, Agent, or Firm*—Greenberg Traurig LLP

(57) ABSTRACT

A composition and method for simultaneously lightening and coloring hair. The composition generally consists of three components, specifically, a bleaching composition, an oxidizing composition and a dyeing composition. The composition preferably lightens hair color by a plurality of levels and simultaneously deposits tones that are attractive and long lasting. In a preferred embodiment, the bleaching composition is a powder composition based on silicate and/or carbonate salts and/or persulfate salts of ammonium, potassium or sodium. The persulfate bleaching composition can be ammonia-free, if desired. The oxidizing composition is preferably an anhydrous hydrogen peroxide solution, or another source of oxygen. The bleaching composition can be mixed with the oxidizing composition to form an anhydrous creme that is applied to the hair.

19 Claims, No Drawings

COMPOSITION AND METHOD FOR SIMULTANEOUSLY LIGHTENING AND COLORING HAIR

1. CROSS REFERENCE TO RELATED APPLICATIONS

This non-provisional patent application claims priority to U.S. Provisional Patent Application Ser. No. 60/758,954, filed Jan. 13, 2006, titled "Composition and Method for Simultaneously Lightening and Coloring Hair," which is incorporated by reference in its entirety.

BACKGROUND OF THE INVENTION

2. Field of the Invention

The present invention relates generally to the coloring of hair, and in particular to a composition and method for simultaneously lightening and coloring hair in a single step using one or more basic dyes.

3. Description of the Related Art

Melanin is a pigment which provides hair with its natural color. Melanin can be found in granular form in the cortex of hair follicles. There are two general classes of melanin pigments: eumelanins and pheomelanins. Eumelanins are brownish-black in hue, while pheomelanins are reddish-orange in hue. Darker hair typically has a higher concentration of eumelanins, while reddish hair typically has a higher concentration of pheomelanins. Light blond hair typically has a low concentration of both pigments.

Dark hair color can be lightened by applying a bleaching agent to the hair to attack and destroy the melanin granules. The bleaching agent typically includes a hydrogen peroxide solution. The hydrogen peroxide solution can be used alone, or in combination with anhydrous powders such as silicate and/or carbonate salts or persulfate salts of ammonium, potassium or sodium. The mixture of hydrogen peroxide and anhydrous powder is beneficial if stronger bleaching is desired, such as, for example, when lifting brown or darker hair to a pale blonde color.

During hair bleaching, pheomelanins are typically more difficult to destroy than eumelanins. As a result, dark hair tends to take on a reddish or orange tone when bleached due to the pheomelanin pigment remaining in the hair. In order to neutralize this reddish or orange tone, colorants or dyes are typically applied to the hair either during or after bleaching.

It is known that certain basic dyes can be combined with a bleaching mixture such that when the combination is applied to the hair, the hair is bleached and toning or coloring is imparted to the hair in a single step. For example, U.S. Pat. No. 6,440,177 to Orr teaches that the basic azo dyes listed in Table 1 below have been found to effectively color bleached hair. The listed dyes have been found to be stable in the bleach mixture and capable of depositing the desired amount of tone on the hair.

TABLE 1

Functioning One-Step Dyes under U.S. Pat. No. 6,440,177

| Dye | Chemical Class | C.I. # | Toning ability/Stability (5 being highest) |
| --- | --- | --- | --- |
| Basic Blue | 41 | Azo | 11154 | 3 |
| Basic Blue | 67 | Azo | 45175 | 4 |
| Basic Brown | 1 | Azo | 21000 | 2 |
| Basic Brown | 4 | Azo | 21010 | 2 |
| Basic Red | 18 | Azo | 11085 | 5 |
| Basic Red | 22 | Azo | 11055 | 4 |
| Basic Red | 46 | Azo | | 5 |
| Basic Red | 104 | Azo | | 5 |
| Basic Violet | 35 | Azo | | 4 |
| Basic Yellow | 45 | Azo | | 2 |
| Basic Yellow | 57 | Azo | | 2 |
| Basic Yellow | 67 | Azo | | 2 |

The Orr patent also teaches that certain other basic azo dyes, for example Basic Blue 54, are not effective as one step colorants, as they are generally unstable in the bleaching mixture and/or ineffective in depositing tone or coloring on the hair.

The dyes listed in Table 1 only represent certain particular shades of the respective colors. As a result, these particular dyes may not produce the desired shade or tone when applied to a person's hair, either alone or in combination with other dyes. This is particularly true when the person's hair has been bleached to a very pale blond shade, such that the tone that results from application of dye is particularly noticeable.

Additionally, even if one or more of the listed dyes in Table 1 provides the desired tone, the dyes may not exhibit the desired colorfastness or purity properties. Further, the dyes may be prohibitively expensive. In addition, it may be necessary to use a selected dye in large amounts or at very high concentrations to achieve the desired tone or colorfastness, which may result in diminished stability of the dye in the bleaching solution.

It would be advantageous to provide a composition and method for hair lightening and coloring in a single step that produces the desired toning and stability characteristics when used in limited amounts and/or at high concentrations in a person's hair. It would also be advantageous to provide a composition and method for hair lightening and coloring that provides the desired shade of color to a person's hair while also being generally stable in a bleach solution and effective in depositing tone on the hair for an extended period of time.

Accordingly, prior to the development of the present invention, there has been no composition and method for hair lightening and coloring in a single step that: provides desired toning and stability characteristics when used in limited amounts and/or at high concentrations; and provides a desired shade of color to hair while being generally stable in a bleach solution and effective in depositing the tone on the hair for an extended period of time. Therefore, the art has sought a composition and method for hair lightening and coloring that exhibits desired toning features and stability, particularly when used in limited amounts and at high concentrations; and provides a desired shade of coloring to hair while being generally stable in the bleach solution and effective in depositing the tone on the hair for an extended period of time.

SUMMARY OF THE INVENTION

In accordance with the invention, the foregoing advantages have been achieved through the present composition for simultaneously lightening and coloring hair. The composition generally consists of three components, specifically, a bleaching composition, an oxidizing composition and a dyeing composition. The composition preferably lightens hair color by a plurality of levels and simultaneously deposits tones that are attractive and long lasting.

In a preferred embodiment, the bleaching composition is a powder composition based on silicate and/or carbonate salts and/or persulfate salts of ammonium, potassium or sodium. The persulfate bleaching composition can be ammonia-free, if desired. The oxidizing composition is preferably an anhydrous hydrogen peroxide solution, or another source of oxygen. The bleaching composition can be mixed with the oxidizing composition to form an anhydrous creme that is applied to the hair. Alternatively, the oxidizing composition can be incorporated into the bleaching composition in a solid form, such as, for example, urea peroxide or sodium percarbonate and potassium percarbonate, and mixed with water or other liquid to activate. The dying composition preferably includes one or more basic azo dyes in an amount sufficient to color hair. The one or more basic azo dyes can include Basic Blue 54 (C.I. #11052). The dyeing composition can also include a combination of Basic Blue 54 with Acid Red 92 (C.I. #45410) to achieve the desired tone and shade.

In accordance with another aspect of the invention, the foregoing advantages have also been achieved through the present method for preparing a composition that simultaneously lightens and colors hair. This aspect of the invention preferably includes the steps of mixing the bleaching composition, the oxidizing composition and the dyeing composition in an amount sufficient to color hair, whereby the dyeing composition includes one or more basic azo dyes. A feature of the invention is that the one or more basic azo dyes can include Basic Blue 54. Another feature of the invention is that Basic Blue 54 can be used in combination with Acid Red 92 to achieve the desired tone and shade.

In accordance with another aspect of the invention, the foregoing advantages have also been achieved through the present method for simultaneously lightening and coloring hair. This aspect of the invention preferably includes the steps of mixing the bleaching composition, the oxidizing composition and the dyeing composition in an amount sufficient to color hair, and applying said mixture to hair. A feature of the invention is that the one or more basic azo dyes can include Basic Blue 54. Another feature of the invention is that Basic Blue 54 can be used in combination with Acid Red 92 to achieve the desired tone and shade. In a preferred embodiment, the bleaching composition, the oxidizing composition and the dyeing composition are mixed together initially, and the mixture is then applied to a person's hair in a single step.

The composition and methods of the present invention, when compared with previously proposed compositions and methods for simultaneously lightening and coloring hair, have the advantages of: providing the desired shade of color to a person's hair, increased stability of the dyeing composition in the bleaching composition when used in limited amounts and/or at high concentrations and improved effectiveness of the dyeing composition in depositing color and tone on the hair for an extended period of time.

While the invention will be described in connection with the preferred embodiment, it will be understood that it is not intended to limit the invention to that embodiment. On the contrary, it is intended to cover all alternatives, modifications, and equivalents as may be included within the spirit and scope of the invention as defined by the claims.

DETAILED DESCRIPTION OF THE INVENTION

The composition of the present invention preferably includes one or more basic azo dyes used alone or in combination with other dyes to achieve the desired tone and shade when applied to a person's hair. In a preferred embodiment, the azo dye is Basic Blue 54, used alone or in combination with other azo dyes, or with Acid Red 92 dye.

Commercial dyes such as Basic Blue 54 and Acid Red 92 are categorized in a Colour Index and identified by a unique Colour Index (C.I.) Constitution Number which indicates the chemical class of the dye. The Colour Index classifies dyes within specific categories along with other dyes having essential colorants of the same chemical constitution and formed from the same single chemical reaction or series of reactions. C.I. Constitution Numbers are generally classified as follows:

| Generic Name of Dye | Constitution Numbers |
| --- | --- |
| Nitroso | 10000-10299 |
| Nitro | 10300-10999 |
| Monoazo | 11000-19999 |
| Disazo | 20000-29999 |
| Stilbene | 40000-40799 |
| Diphenylmethane | 41000-41999 |
| Triarylmethane | 42000-44999 |
| Xanthene | 45000-45999 |
| Acridine | 46000-46999 |
| Quinoline | 47000-47999 |
| Methine | 48000-48999 |
| Thiazole | 49000-49399 |
| Indamine | 49400-49699 |
| Indophenol | 49700-49999 |
| Azine | 50000-50999 |
| Oxazine | 51000-51999 |
| Thiazine | 52000-52999 |
| Aminoketone | 56000-56999 |
| Anthraquinone | 58000-72999 |
| Indigoid | 73000-73999 |
| Phthalocyanine | 74000-74999 |
| Inorganic Pigments | 77000-77999 |

C.I. Basic Blue 54 has the Colour Index Constitution Number 11052, which indicates that it is a monoazo or "azo" dye. The dye has a bright blue shade and the chemical structure is shown below.

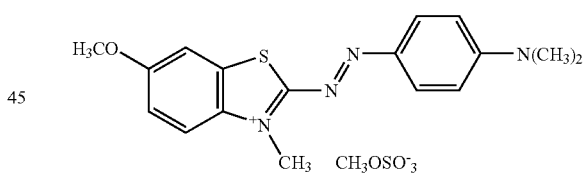

C.I. Basic Blue 54 advantageously remains stable when added to the bleaching composition. More specifically, Basic Blue 54 does not oxidize when mixed with the bleaching composition under test conditions, e.g., three months in the composition at 40 degrees Celsius. Basic Blue 54 is also advantageously effective in depositing color or tone on the bleached hair. More specifically, the bright blue shade of the Basic Blue 54 dye attaches to, and does not disappear from, the hair to provide noticeable darkened tone to the bleached hair.

Basic Blue 54 can be used as the sole means for providing color or tone to hair. For example, Basic Blue 54 can be used to replace some or all of the pigments which are typically used in hair colorant compositions. The composition of the present invention containing Basic Blue 54 can be utilized in either water-based or anhydrous, nonwater-based hair coloring systems. Anhydrous systems are utilized, for example, when chemicals which are reactive with water such as potassium persulfate, are present in the composition. According to an embodiment of the present invention, isododecane is utilized as a preferred solvent in an anhydrous system.

C.I. Acid Red 92 (also known as Phloxine B) is a xanthene dye with a C.I. number of 45410. The empirical formula is $C_{20}H_2Br_4Cl_4Na_2$. The dye has a bright pink shade and the chemical structure is shown below.

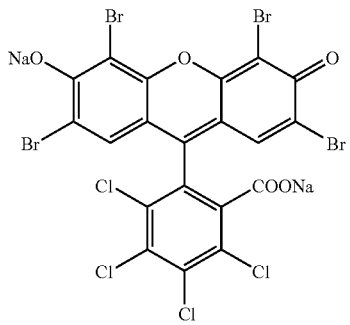

Acid Red 92 also advantageously remains stable and does not react with the bleaching composition under test conditions, e.g., after three months at 40 degrees Celsius. Further, Acid Red 92 is effective in depositing color or tone on the bleached hair when combined with Basic Blue 54.

Acid Red 92 advantageously does not react with Basic Blue 54 when the two dyes are combined according to the present invention. The bright pink and bright blue shades of the dyes combine to form a purplish shade. The combination of dyes attaches to, and does not disappear from, the hair and provides a darkened tone to the hair that is noticeable, but less pronounced than the darkening found by using the Basic Blue 54 dye alone.

The composition of the present invention also advantageously produces the desired toning and stability characteristics when used in limited amounts and/or at high concentrations in a person's hair. Preferably, a hydrogen peroxide-persulfate mix is utilized as the bleaching agent. The hydrogen peroxide-persulfate can lift the hair color to extremely high levels when the components are mixed in appropriate percentages and applied to the hair in sufficient quantities and for an adequate time period. Once the hair has been lifted to these higher levels of color, the application of the Basic Blue 54 dye gives the hair the desired shade or tone or color.

The following examples are meant to illustrate embodiments of the invention in detail, but are in no way meant to limit the scope of the invention.

EXAMPLE 1

The following components were mixed to form a composition according to the present invention which is effective in depositing color on the hair and lifting the hair color by multiple levels, e.g., from a dark black to a medium or "cool" blonde:

| Raw Material | Percentage |
| --- | --- |
| Mineral Oil | 16.5% |
| Basic Blue 54 | 0.336% |
| Acid Red 92 | 0.0015% |
| Blue "100%" pigment | 0.05% |

-continued

| Raw Material | Percentage |
| --- | --- |
| VERSAGEL ™ M 1600 | 6.00% |
| Lightening Powder ($H_2O_2$) | 63.2% |
| Potassium Persulfate (granular) | 10.41% |
| Sodium Metasilicate Anhydrous | 1.54% |
| GRANACRYSIL ™ BMAS | 2.00% |
| Biocera | 0.0001% |
| Tetrasodium EDTA (Sequestrene 220) | — |

The mineral oil and dyes were mixed in the approximate percentages listed until completely dispersed. The pigments were added and mixed until homogenous. The Versagel M 1600 and Lightening powder were then added and mixed. The remaining components were then added and mixed for approximately one hour. The resulting composition was a light blue cream with a pH of 10-11 and a viscosity of 40,000-45,000 at 25 degrees Celsius.

EXAMPLE 2

The following components were mixed to form a composition according to the present invention which is effective in depositing color on the hair and lifting the hair color by multiple levels, e.g., from a dark black to a lighter or "beige" blonde:

| Raw Material | Percentage |
| --- | --- |
| Mineral Oil | 2.66% |
| Basic Blue 54 | 0.16% |
| Acid Red 92 | 0.0021% |
| Blue "100%" pigment | 0.05% |
| Violet "100%" pigment | 0.05% |
| VERSAGEL ™ M 1600 | 11.026% |
| Lightening Powder ($H_2O_2$) | 53.72% |
| Potassium Persulfate (granular) | 9.89% |
| Sodium Metasilicate Anhydrous | 1.463% |
| GRANACRYSIL ™ BMAS | 2.00% |
| Biocera | 0.0001% |
| Tetrasodium EDTA (Sequestrene 220) | 1.349% |

The mineral oil and dyes were mixed using homogenizer until completely dispersed. The pigments were added and mixed until homogenous. The Versagel M 1600 and Lightening powder were then added and mixed. The remaining components were then added and mixed for approximately one hour. The resulting composition was a light blue/violet cream with a pH of 10-11 and a viscosity of 40,000-45,000 at 25 degrees Celsius.

It is to be understood that the invention is not limited to the exact details of construction, operation, exact materials, or embodiment shown in described, as obvious modifications and equivalents will be apparent to one skilled in the art, or technological field. For example, other dyes such as, for example, Basic Red 54, may also be utilized in the composition of the present invention. Accordingly, the invention is therefore to be limited only by the scope of the appended claims in a yet to be filed non-provisional application.

The invention claimed is:

1. A method of simultaneously lightening and coloring hair, the method comprising: mixing a bleaching composition present in an amount sufficient to lighten the color of hair, an oxidizing composition, a dyeing composition including Basic Blue 54 azo dye that remains stable when added to the bleaching composition and deposits color on the hair, a mineral oil composition and a gelled thickening agent; and applying the mixture to hair to lighten and color the hair in a single step.

2. The method of claim 1, wherein the dyeing composition include Acid Red 92 dye.

3. A hair colorant composition for simultaneously lightening and coloring hair, the composition comprising: a bleaching component; a dyeing component including Basic Blue 54 azo dye that remains stable when added to the bleaching composition and deposits color on the hair; an oxidizing component; a mineral oil component; and a gelled thickening agent component.

4. The composition of claim 3, wherein the bleaching component includes one or more salts from the group consisting of silicate and carbonate.

5. The composition of claim 3, wherein the bleaching component includes one or more persulfate salts from the group consisting of ammonium, potassium and sodium.

6. The composition of claim 3, wherein the bleaching component is ammonia-free.

7. The composition of claim 3, wherein the oxidizing component includes hydrogen peroxide.

8. The composition of claim 3, wherein the dyeing component further includes Acid Red 92 dye.

9. The composition of claim 3, wherein the composition is anhydrous.

10. The composition of claim 3, wherein the bleaching component is mixed with the oxidizing component to form an anhydrous creme.

11. The composition of claim 3, wherein the bleaching component is a hydrogen peroxide-persulfate mix.

12. A method of forming a hair colorant composition for simultaneously lightening and coloring hair, the method comprising the steps of: dissolving Basic Blue 54 in a mineral oil composition in an amount sufficient to color hair; adding a gelled thickening agent to the mineral oil composition to form a dyeing composition; and adding a bleaching agent to the dyeing composition to form a bleaching composition, wherein the dyeing composition is stable in the bleaching composition.

13. The method of claim 12, further comprising the step of: mixing the bleaching composition with an oxidizing composition.

14. The method of claim 12, further comprising the step of dissolving a xanthene dye in the mineral oil composition.

15. The method of claim 14, wherein the xanthene dye is Acid Red 92.

16. The method of claim 12, wherein the bleaching composition has a pH in the range from 10-11.

17. The method of claim 12, further comprising isododecane as a solvent.

18. The method of claim 12, wherein the gelled thickening agent is transparent and based from nonpolar oils.

19. The method of claim 12, wherein the gelled thickening agent is an ethylene/propylene copolymer.

* * * * *